US008052668B2

(12) United States Patent
Sih

(10) Patent No.: US 8,052,668 B2
(45) Date of Patent: Nov. 8, 2011

(54) NEUROTOXIC AGENTS AND DEVICES TO TREAT ATRIAL FIBRILLATION

(75) Inventor: Haris J. Sih, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 485 days.

(21) Appl. No.: 11/383,095

(22) Filed: May 12, 2006

(65) Prior Publication Data

US 2006/0282120 A1  Dec. 14, 2006

Related U.S. Application Data

(60) Provisional application No. 60/680,800, filed on May 13, 2005.

(51) Int. Cl.
  *A61M 31/00* (2006.01)
  *A61M 29/00* (2006.01)
  *A61N 1/00* (2006.01)
(52) U.S. Cl. ............... 604/509; 604/101.01; 604/96.01; 607/2
(58) Field of Classification Search ............ 604/101.01–101.05, 509; 607/2
See application file for complete search history.

(56) References Cited

U.S. PATENT DOCUMENTS

| 5,328,471 A * | 7/1994 | Slepian ..................... 604/101.03 |
| 5,728,068 A * | 3/1998 | Leone et al. ............. 604/101.01 |
| 5,766,152 A | 6/1998 | Morley et al. |
| 5,919,163 A * | 7/1999 | Glickman ................ 604/101.05 |
| 5,947,952 A | 9/1999 | Morley et al. |
| 6,113,584 A | 9/2000 | Morley et al. |
| 2003/0065240 A1 | 4/2003 | Sanders et al. |
| 2003/0069606 A1* | 4/2003 | Girouard et al. .................. 607/3 |
| 2005/0171575 A1* | 8/2005 | Dev et al. .......................... 607/2 |

OTHER PUBLICATIONS

Ahmed, J., et al., "Three-dimensional analysis of pulmonary venous ostial and antral anatomy: implications for balloon catheter-based pulmonary vein isolation.", J Cardiovasc Electrophysiol., 17(3), (Mar. 2006), 251-5.
Goldstein, J. A, et al., "Comparison of the diameter consistency and dilating force of the controlled radial expansion balloon catheter to the conventional balloon dilators.", Am J Gastroenterol., 95(12), (Dec. 2000), 3423-7.
Haines, D. E, "With pulmonary vein isolation for paroxysmal atrial fibrillation ablation, one size does not fit all.", J Cardiovasc Electrophysiol., 13(10), (Oct. 2002), 962-3.
Lesh, M. D, et al., "An anatomic approach to prevention of atrial fibrillation: pulmonary vein isolation with through-the-balloon ultrasound ablation (TTB-USA).", Thorac Cardiovasc Surg., 47 (Suppl 3), (Aug. 1999), 347-51.
Mansour, M., et al., "Assessment of pulmonary vein anatomic variability by magnetic resonance imaging: implications for catheter ablation techniques for atrial fibrillation.", J Cardiovasc Electrophysiol., 15(4), (Apr. 2004), 387-93.
Ready, Vivek Y., et al., "Balloon catheter ablation to treat paroxysmal atrial fibrillation: What is the Level of pulmonary venous isolation?", Heart Rhythm, 5(3), (Mar. 2008), 353-360.

(Continued)

*Primary Examiner* — Nicholas D Lucchesi
*Assistant Examiner* — Rebecca E Eisenberg
(74) *Attorney, Agent, or Firm* — Schwegman, Lundberg & Woessner, P.A.

(57) ABSTRACT

Devices and methods to treat atrial fibrillation via inhibition of nerves which innervate the pulmonary vein are provided.

14 Claims, 12 Drawing Sheets

OTHER PUBLICATIONS

Saliba, Wilber W., et al., "Circumferential ultrasound ablation for pulmonary vein isolation: analysis of acute and chronic failures", J. Cardiovasc. Electrophysiol, Abstract, (Oct. 2002) 1 page.

Seshadri, N., et al., "Pulmonary vein isolation for treatment of atrial fibrillation: recent updates.", Pacing Clin Electrophysiol., 26(7 Pt 2), (Jul. 2003), 1636-40.

* cited by examiner

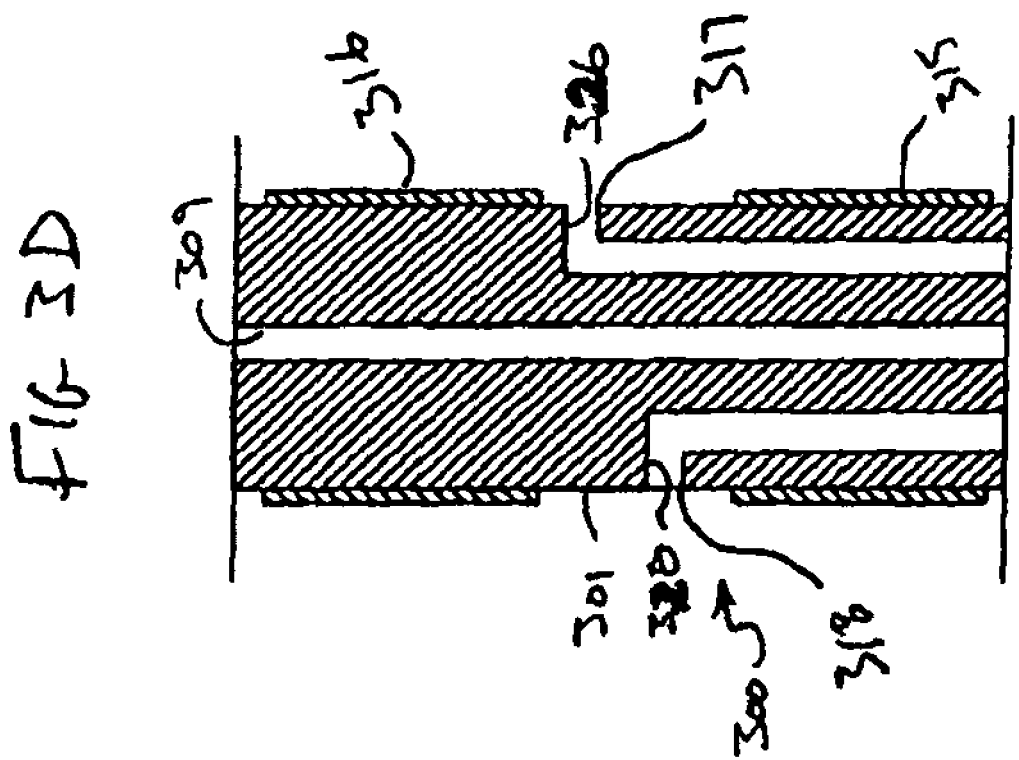

NEUROTOXIC AGENTS AND DEVICES TO TREAT ATRIAL FIBRILLATION

CROSS-REFERENCE TO RELATED APPLICATION(S)

This application claims the benefit of U.S. Provisional Application No. 60/680,800, filed on May 13, 2005, under 35 U.S.C. §119(e), which is hereby incorporated by reference.

TECHNICAL FIELD

This patent document pertains generally to apparatus and methods to inhibit or treat atrial fibrillation, and, more particularly, to the use of an apparatus to deliver agents including neurotoxic agents to inhibit or treat atrial fibrillation.

BACKGROUND

Fibrillation refers to a condition in which muscle fibrils enter a state of extremely rapid, small-scale contractions that do not coordinate to affect contraction of the muscle as a whole. When this occurs in the left ventricle (LV), the heart chamber responsible for pumping blood into the arterial vasculature, it is serious and rapidly fatal. Atrial fibrillation (AF), fibrillation which occurs in the musculature of the atria and affects as many as 2 million Americans, is less immediately serious and not necessarily fatal. It is still important to treat AF, however, for several reasons. First, AF is associated with a loss of atrio-ventricular synchrony which can be hemodynamically compromising and cause such symptoms as dyspnea, fatigue, vertigo, and angina. AF can also predispose to stroke or cerebral vascular accidents resulting from emboli forming in the left atrium. Although drug therapy, in-hospital cardioversion, and implantable cardioverter/defibrillators are acceptable treatment modalities for AF, a curative approach offers a number of advantages to certain patients, including convenience and greater efficacy.

One such approach is ablation therapy which treats cardiac arrhythmias by destroying myocardial tissue involved in the initiation or maintenance of the tachyarrhythmia. Linear ablation in the right atrium (RA) and/or left atrium (LA) was initially proposed with the purpose of replicating the surgical "maze" procedure (Cox et al., *Ann. Thoracic Surg.*, 56:814 (1993)). However, ablation is most often accomplished by delivering radiofrequency (RF) electrical energy to a catheter electrode that has been placed next to the tissue to be destroyed after identifying ectopic sites or reentrant pathways, e.g., by mapping electrical activation of the atria.

Recent evidence has shown that a high percentage of paroxysms of AF are initiated by trains of rapid discharges originating from the pulmonary veins (PVs) of the LA, and it has been suggested that the autonomic nervous system may play a role in the generation of the ectopic foci in the pulmonary vein, at least in a canine model (Schauerte et al., *J. Cardiovasc. Electrophysiol.*, 12:592 (2001)). Accordingly, catheter techniques have been developed for ablating these sites with RF energy applied from within the PVs. Selective ablation of arrhythmogenic foci, mainly located within the PVs, was reported as an effective treatment for AF (Haissaguerre et al., *NEJM*, 339:659 (1998)). Another ablation technique involves the production of a circumferential ablation lesion within a PV in order to block the conduction pathway from the vein to the LA, e.g., a circumferential conduction block at the pulmonary vein ostia (Pappone et al., *Circ.*, 102:2619 (2000); Pappone et al., *Circ.*, 109:327 (2004)). However, an effective circumferential lesion must be completely circular. A contiguous line of conduction block may be created from a series of discrete circular RF lesions, or 'spot welds' (Schwartzman, *PACE*, 22:711(1999)). Nevertheless, spot welding is tedious and may be ineffective because the creation of a contiguous circumferential lesion from a series of precisely placed individual RF lesions is difficult to achieve under current imaging limitations of x-ray fluoroscopy as well as other imaging modalities. Moreover, common complications of ablation procedures include thrombus formation, pulmonary venous stenosis, and atrio-esophageal fistula formation. Furthermore, the success rates for pulmonary vein ablation are around 70%, indicating that other mechanisms are involved in AF.

What is needed is an improved method to inhibit AF, e.g., originating from ectopic sites.

SUMMARY OF THE INVENTION

The present invention provides an apparatus and methods to inhibit and/or treat atrial fibrillation, e.g., atrial fibrillation resulting from electrical discharges from ectopic foci in one or more pulmonary veins, including paraoxysmal atrial fibrillation. The apparatus delivers and the methods employ at least one agent that inhibits or eliminates neuronal electrical activity, i.e., the agent is a neurotoxic agent and optionally is neurolytic. In one embodiment, the agent is an autonomic nervous system (ANS) neurotoxin and may be capable of irreversibly damaging axonal membranes. In contrast to electrical ablation, which produces lesions in the exposed tissue, the present invention may have a lower risk for stenosis and thrombosis.

In one embodiment, a neurotoxic agent is administered transthoracically to the exterior of a pulmonary vein or ostium thereof in an amount effective to reduce the number (frequency) of electrical discharges from one or more ectopic foci, and/or reduce the number of ectopic foci, in one or more pulmonary veins from reaching the atrium. In another embodiment, an intravascular device, e.g., a catheter, is introduced to a pulmonary vein or ostium of the vein, for instance, via an endocardial approach, and a neurotoxic agent is administered via the device in an amount effective to reduce the number (frequency) of electrical discharges from one or more ectopic foci, and/or reduce the number of ectopic foci, in one or more pulmonary veins from reaching the atrium. Thus, neurotoxic agent administration electrically isolates the pulmonary vein from the atrium, which interrupts an electrical conduction pathway between the vein and the atrium, thereby inhibiting or treating atrial fibrillation associated with one or more ectopic foci in the pulmonary vein. In one embodiment, a catheter is employed to administer the neurotoxic agent to an impeded flow vein. In one embodiment, flow in and out of the vein is impeded by two or more occlusion balloons prior to delivery of the neurotoxic agent via ports or holes in the catheter and/or a balloon thereof. In one embodiment, the device is a balloon catheter, placed in or near the pulmonary vein or ostium thereof, such as one with occlusion balloons at proximal and distal ends of the catheter.

In one embodiment, a balloon catheter is introduced into a blood vessel of a mammal and positioned in or near a region suspected of having one or more ectopic foci. The invention includes identifying one or more ectopic foci in a region of one or more pulmonary veins in a mammal such as a mammal having, or at risk of having, arrhythmias, using a catheter having at least one expandable electrode that is expanded from the catheter body. Once the electrode is expanded so as to be in contact with the vessel wall, high frequency stimulation, e.g., 100 to 250 Hz and in one embodiment about 200

Hz, is applied to the vessel wall via the electrode and heart rate and/or blood pressure detected or determined from implanted sensors or external instruments. Once a region is identified where high frequency stimulation results in altered heart rate and/or blood pressure, or where high frequency stimulation does not alter heart rate and/or blood pressure, the high frequency stimulation is discontinued. To isolate a region where high frequency stimulation results in altered heart rate and/or blood pressure, balloons of the catheter are inflated to create a chamber, e.g., approximately 1 inch in length. The blood in the chamber created by balloon inflation is optionally replaced with a nontoxic, physiological compatible solution other than blood, e.g., a saline or a radiopaque contrast solution. Baseline heart rate and/or blood pressure are detected or determined, and optionally recorded. Optionally, after detecting or determining baseline heart rate and/or blood pressure, the region is subjected to high frequency stimulation by one or more expanded electrodes, e.g., the electrode(s) may be reexpanded if previously contracted, and changes in heart rate and/or blood pressure detected or determined, and optionally recorded. A neurotoxic agent is introduced into the chamber created by balloon inflation, e.g., a neurotoxic solution replaces blood or another nontoxic physiological compatible solution, and heart rate and/or blood pressure detected or determined. The region may be subjected to high frequency stimulation by one or more expanded electrodes prior to and during neurotoxic agent administration, or after the neurotoxic agent is introduced to the chamber created by the balloons, and optionally during detecting or determining whether heart rate and/or blood pressure have normalized. If the detected or determined heart rate and/or blood pressure are not normalized after neurotoxic agent administration relative to baseline, the duration of contact of the vessel with the neurotoxic agent may be extended, the neurotoxic agent may be replaced with a different neurotoxic agent, or the neurotoxic agent may be replaced with the same neurotoxic agent, e.g., at the same or a different concentration. Once heart rate and/or blood pressure are normalized, in one embodiment, the neurotoxic agent is replaced with a nontoxic, physiologically compatible solution that is not blood, for instance, saline, the balloons are deflated and the catheter is removed. In another embodiment, the neurotoxic agent is replaced with blood, e.g., by deflating the two balloons, and the catheter is removed. In one embodiment, a mammal to be treated for atrial fibrillation may have been previously treated for atrial fibrillation with other therapies including chemical therapy and/or electrical ablation therapy.

Also provided is an apparatus for treating atrial fibrillation. In one embodiment, the apparatus includes one or more electrodes. In one embodiment, the apparatus includes a balloon catheter adapted for delivering one or more agents to a pulmonary vein, which balloon catheter includes two or more balloons and one or more expandable electrodes. In one embodiment, the apparatus includes a stent functioning as an electrode. For instance, the apparatus may be a stent catheter having a stent functioning as an electrode which is mounted on the catheter for deployment in a pulmonary vein, the catheter including a balloon at its distal end, another for expanding the stent within a pulmonary vein, and yet another at its proximal end. In another embodiment, the catheter includes a balloon at its distal end for expanding within a pulmonary vein and another at its proximal end for expanding within an atrium or pulmonary vein.

BRIEF DESCRIPTION OF THE FIGURES

FIGS. 3A-3D illustrate lumens extending through a catheter.

DETAILED DESCRIPTION OF THE INVENTION

Figure 1A:
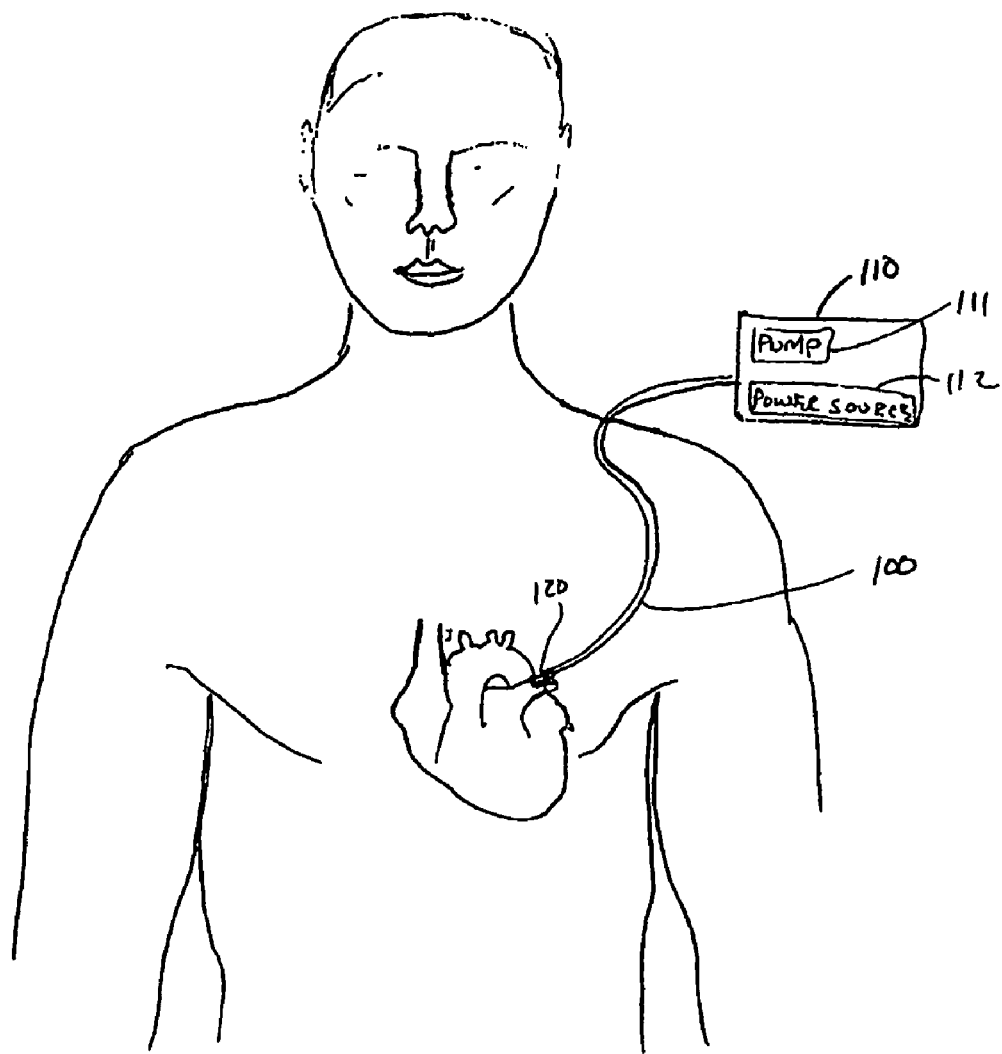
FIG. 1A shows a system for delivering a neurotoxic therapy to treat atrial fibrillation.

Ectopic foci responsible for many episodes of atrial fibrillation are found in the great veins of the atrium known as the pulmonary veins. In order to block electrical discharges from those foci, one or more agents are employed to inhibit or eliminate innervation of those foci and thereby inhibit or eliminate electrical discharges therefrom in the pathway leading from the one or more foci to the atrium. Agents useful in the apparatus and methods of the invention include but are not limited to those which inhibit neural cells, e.g., and preferably have limited cytotoxic effects on other cell types, e.g., vascular endothelial cells, vascular smooth muscle cells, myocytes, myofibroblasts and the like. The neuroinhibitory activity of an agent may be tested in vitro, e.g., using neuronal differentiated stem cells or neuronal cell cultures, e.g., primary neuronal cell cultures, and optionally comparing the activity of the agent on neuronal cells to nonneuronal cells. Once a candidate agent is identified by in vitro methods, it may be tested in animal models. For example, to determine the extent of denervation in vivo, electrical measurements are conducted pre- and post-agent administration to determine when electrical isolation is accomplished.

In one embodiment, an agent useful in the apparatus and methods of the invention includes but is not limited to a neurotoxic agent including a neurolytic agent, and in particular a local anesthetic, e.g., phenol or a derivative thereof, e.g., propofol analogs, including those described in Krasowsky et al. (*J. Med. Chem.*, 45:3210 (2002)), lidocaine; bupivicaine; ambucaine; benzocaine; butamben; procaine; oxybuprocaine; tetracaine; etidocaine; propranolol, prilocaine, mepiracaine, tocainides, and cocaine; bufotoxins; picrotoxin; botulinum toxin or toxic portions thereof; tetrodotoxin; snake venom toxins such as bungarotoxin; dinoflagellate toxins such as those produced by *Pfiesteria pisicida*; gamma-aminobutyric acid; norepinephrine; TNF-α, levodopa/carbidopa; benzodiazepines; 4-aminopyridine; a nerve gas, e.g., soman nerve gas; and pilocarpine. In other embodiments, the agent is a metal, e.g., aluminum, manganese or zinc, a chemotherapeutic agent, such as an alkylating agent, e.g., ifosfamide, paclitaxel, busulfan, platinum, aracytine, or methotrexate, ethanol, propanol, acetaldehyde, acreolin, kainic acid, or glycerol.

Administration of an agent in accordance with the present invention may be continuous or intermittent, depending, for example, upon the recipient's physiological condition, whether the purpose of the administration is therapeutic or prophylactic, and other factors known to skilled practitioners. The administration of the agent may be essentially continuous over a preselected period of time or may be in a series of spaced doses. Moreover, the administration of the agent preferably does not damage the pulmonary vein.

One or more suitable unit dosage forms comprising the agent, which may be formulated for sustained release, can be administered by a variety of routes including intravenous, endocardial and transthoracic routes. The agent may be combined with a pharmaceutically acceptable carrier, diluent or excipient to form a pharmaceutical formulation, preferably in unit dosage form. The total active ingredients in these formulations can comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof.

Pharmaceutical formulations containing the agent can be prepared by procedures known in the art using well known and readily available ingredients. For example, an agent can be formulated with common excipients, diluents, or carriers, and formed into tablets, capsules, suspensions, powders, and the like. Examples of excipients, diluents, and carriers that are suitable for such formulations include the fillers and extenders; binding agents; moisturizing; disintegrating agents; agents for retarding dissolution; resorption accelerators; surface active agents; adsorptive carriers; and lubricants. The formulations can include buffering agents as well as inactive ingredients.

In the practice of certain embodiments of the present invention, the agent is dispersed in a pharmaceutically acceptable carrier that is in liquid phase, and delivered via an implantable device, e.g., a catheter. Useful pharmaceutically acceptable carriers for these purposes include generally employed carriers, such as phosphate buffered saline solution, water, emulsions (e.g., oil/water and water/oil emulsions) and wetting agents of various types.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents, e.g., acetone, ethanol, isopropyl alcohol, glycol ethers, polyglycols and polyethylene glycols, $C_1$-$C_4$ alkyl esters of short-chain acids, preferably ethyl or isopropyl lactate, fatty acid triglycerides, isopropyl myristate, animal, mineral and vegetable oils and polysiloxanes.

The local delivery of the agents of the invention can be by a variety of techniques which administer the agent at or near ectopic sites. Examples of site-specific or targeted local delivery techniques are not intended to be limiting but to be illustrative of the techniques available. Examples include local delivery catheters, such as an infusion catheter, an indwelling catheter, or a needle catheter, synthetic grafts, wraps, shunts and stents or other implantable devices, site specific carriers, direct injection, or direct applications. Local delivery by an implant includes surgical placement of a matrix that contains the agent near the ectopic site(s). The implanted matrix releases the agent by diffusion, chemical reaction, or solvent activators.

In an embodiment, a catheter is employed to deliver an agent to a pulmonary vein. FIG. 1A shows a catheter 100 coupled to a device 110 and extending into a pulmonary vein. In an example, the catheter extends into a pulmonary vein near a patient's heart 120. In an example, the device 110 includes a pump 111 for circulating an agent through the catheter. In an example, the device also includes a power source 112 and control circuitry for delivering an electric signal through the catheter. In an example, the device also includes a processor for analyzing an intrinsic electric heart signal or other data received from one or more physiologic sensors. In an example, the pump and circuitry are both contained in the same device 110. In an alternative example, the pump and circuitry are contained in separate devices.

Figure 1B:
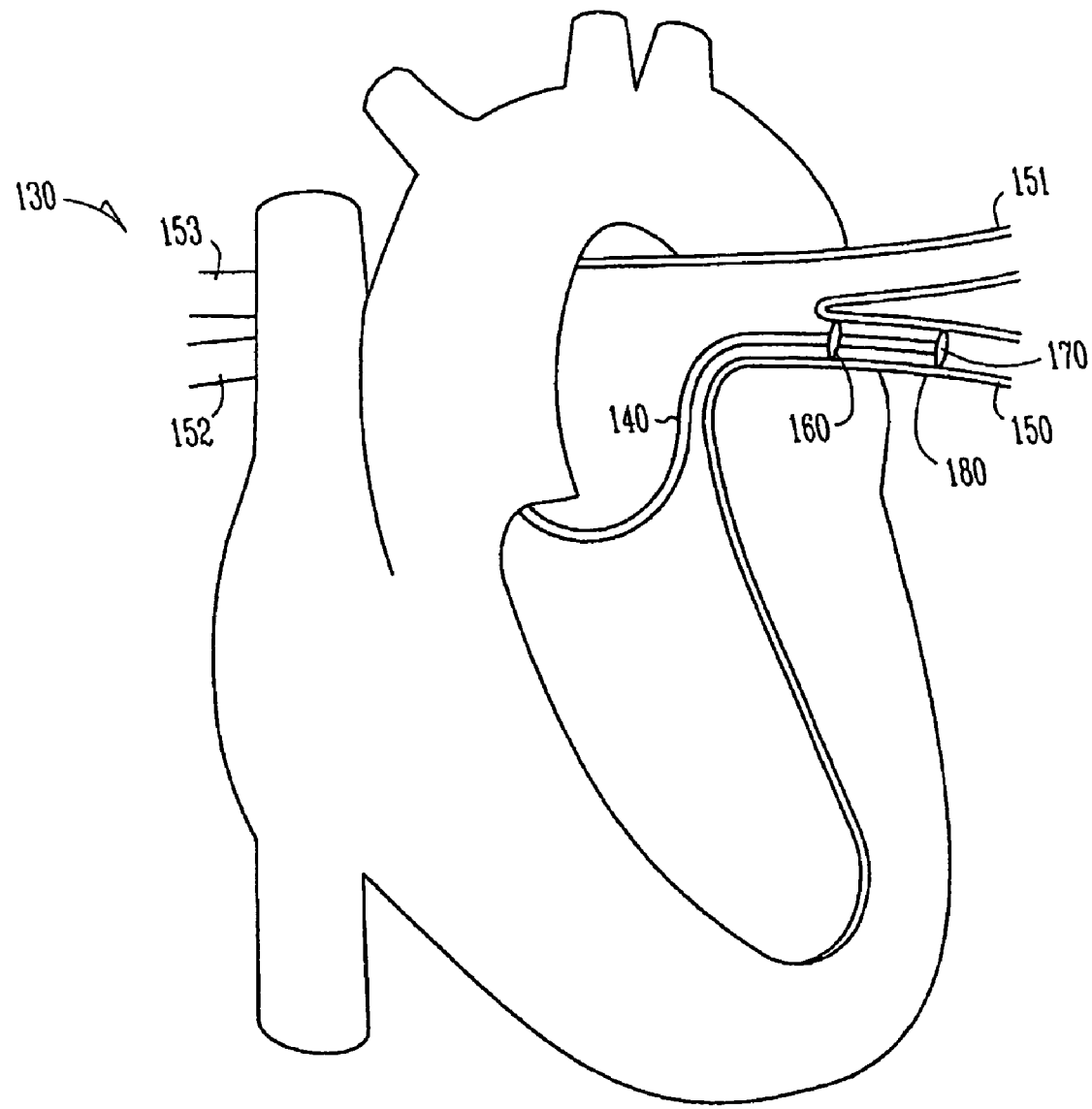
FIG. 1B shows a catheter apparatus and a heart.

FIG. 1B shows a heart 130 and a balloon catheter 140 extending into a left pulmonary vein 150. The catheter includes a pair of balloons 160, 170 that isolate a segment 180 of the pulmonary vein 150 for chemical neurolysis. In an alternative example, the catheter is inserted into the other left pulmonary vein 151, or one of the right pulmonary veins 152, 153. In one example, the catheter is inserted into the aorta and extended through the heart into a pulmonary vein. In an example, the catheter includes a guide wire that allows the catheter to be guided, inserted, or positioned in a pulmonary vein.

Figure 2A:
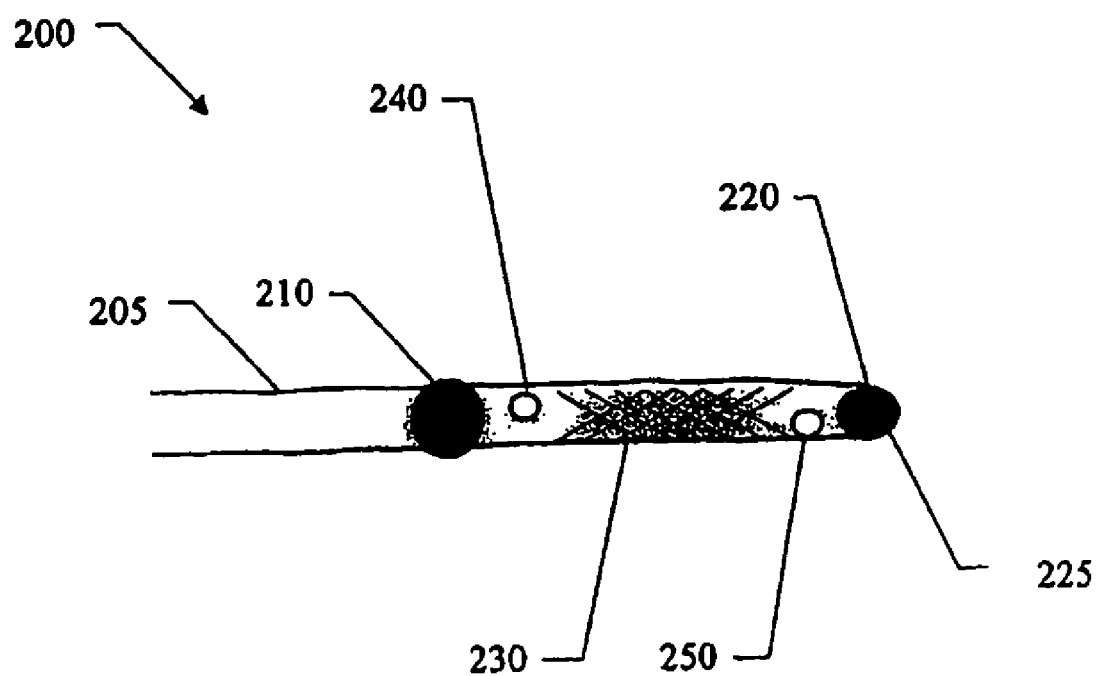
FIG. 2A is an illustration of a balloon catheter with a drug delivery depot.

Referring now to FIG. 2A, another example of a catheter 200 for delivering an agent is shown. The catheter 200 includes a catheter body 205, a first occlusion balloon 210 coupled to the catheter body, and a second occlusion balloon 220 that is spaced from the first occlusion balloon 210 along the catheter body 205. In an example, the second occlusion balloon 220 is located at a distal end 225 of the catheter body 205. The occlusion balloons are inflatable, as shown in FIGS. 2C and 2E. In one embodiment, a first port 240 and a second port 250 are located between the two balloons 210, 220. The first port 240 and second port 250 are in communication with one or more lumens in the catheter body 200. In an example, ports 240, 250 are connected to separate lumens. An example lumen configuration is illustrated in FIGS. 3A-3D. In an alternative example, the catheter includes a single port for delivering and removing the agent.

Returning to FIG. 2A, in an example, an expandable electrode 230 is located between the balloons 210, 220. The expandable electrode is coupled to a conductor that extends on or through the catheter body 205. In an example, a mesh or stent on catheter 200 functions as the expandable electrode 230. A mechanism is configured to expand the stent. In an example, a tensioning mechanism applies a tension to the stent to expand the stent to the intravascular wall of a pulmonary vein. In another example, a balloon is inflated to expand the stent. The expandable electrode 230 is connected to circuitry that is configured to send electrical stimulation signals to the electrode. In an example, the circuitry is configured to apply high frequency stimulation through the electrode.

Figure 2B:
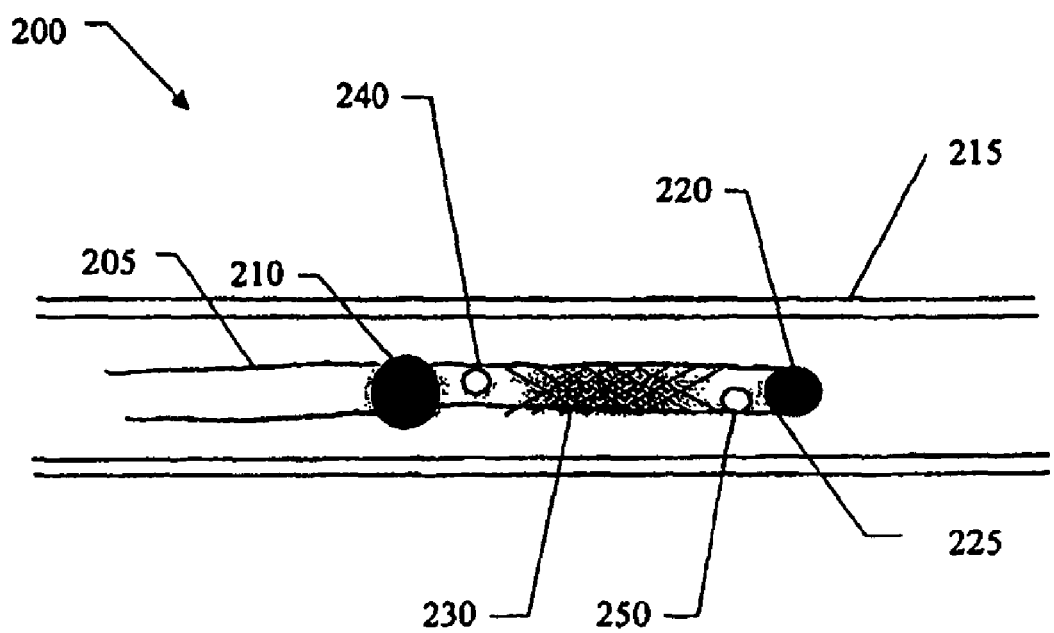
FIGS. 2B and 2C are illustrations of a balloon catheter in a blood vessel.
Figure 2C:
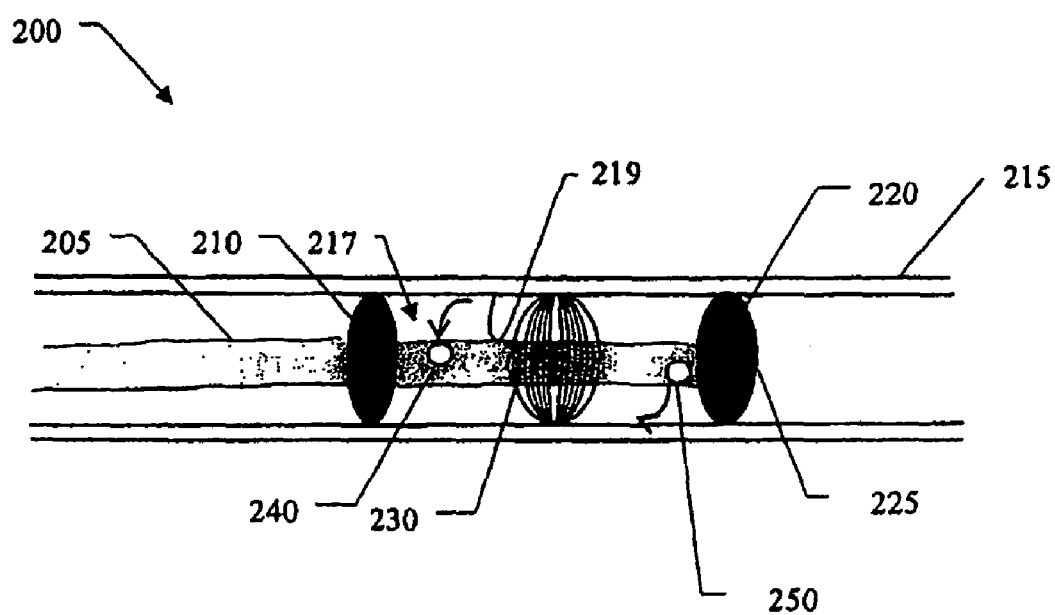

FIGS. 2B and 2C show the catheter 200 configured in a blood vessel 215. In an example, the blood vessel is a pulmonary vein. In FIG. 2B, the first balloon 210, second balloon 220, and expandable electrode 230 are shown in a contracted configuration. In an example, the catheter can be guided through blood vessels or the heart when the balloons and expandable electrode are contracted. FIG. 2C shows the catheter in the blood vessel 215 with the first balloon 210, second balloon 220, and expandable electrode in an expanded configuration. In an example, the balloons are expanded by inflation with a liquid or gas. The first and second balloons 210, 220 block off a portion of the blood vessel lumen 217 between the balloons. In an example, the catheter 200 is configured to selectively circulate one or more fluids such as blood, saline, and/or an agent of the invention which is in solution into and out of the vessel lumen through one or more ports. In an example, the lead 200 is configured to circulate fluid out of the second port 250 into the vessel lumen 217, and out of the vessel lumen into the first port 240. In another example, one type of fluid is circulated through port 240 and a second type of fluid is circulated through second port 250. In an example, the blood vessel is a pulmonary vein. In an example, blood in the vessel between the first and second balloons 210, 220 is replaced by a saline solution or radiopaque contrast solution. In an example, the catheter is configured to circulate an agent, e.g., a neurotoxic solution. In an example, a neurotoxic solution is circulated into the vessel lumen through the first port 240 and out of the vessel lumen through the second port 250. In an example, the expandable electrode 230 delivers a stimulation signal to an intravascular surface 219 of the vein 215. In an alternative example, where the catheter includes a single port, solution is circulated in and out of the vessel through the single port.

Figure 2D:
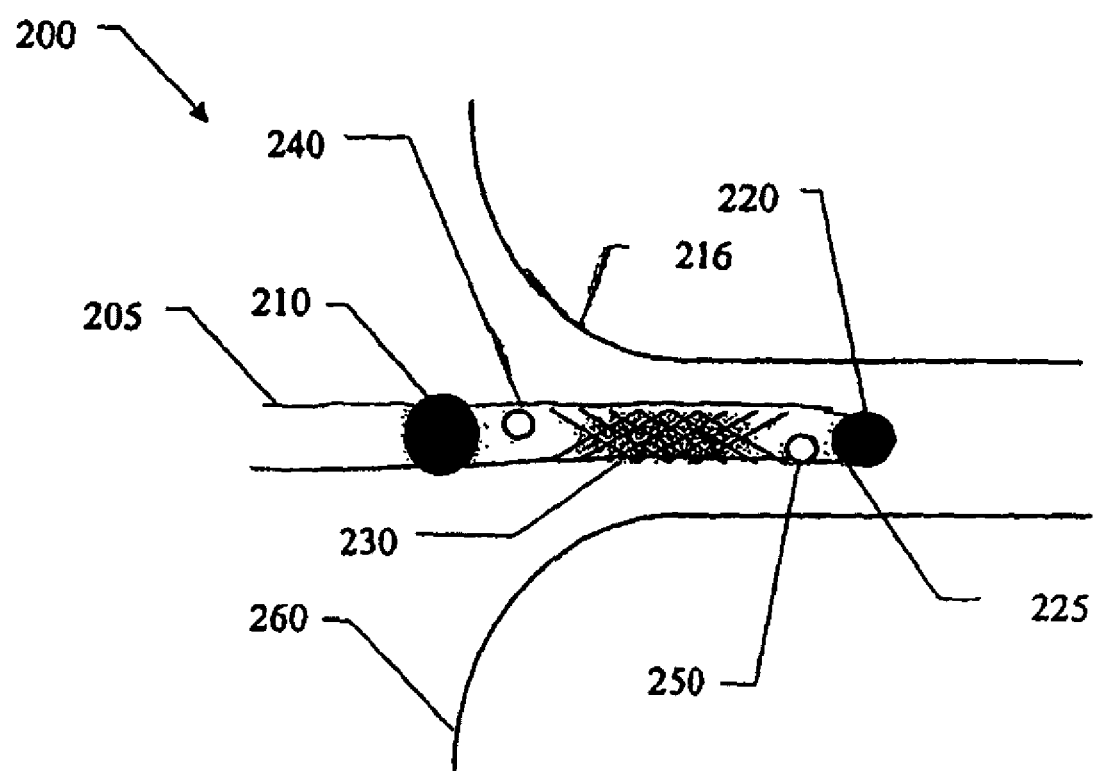
FIGS. 2D and 2E are illustrations of a balloon catheter in a left atrium and pulmonary vein.
Figure 2E:
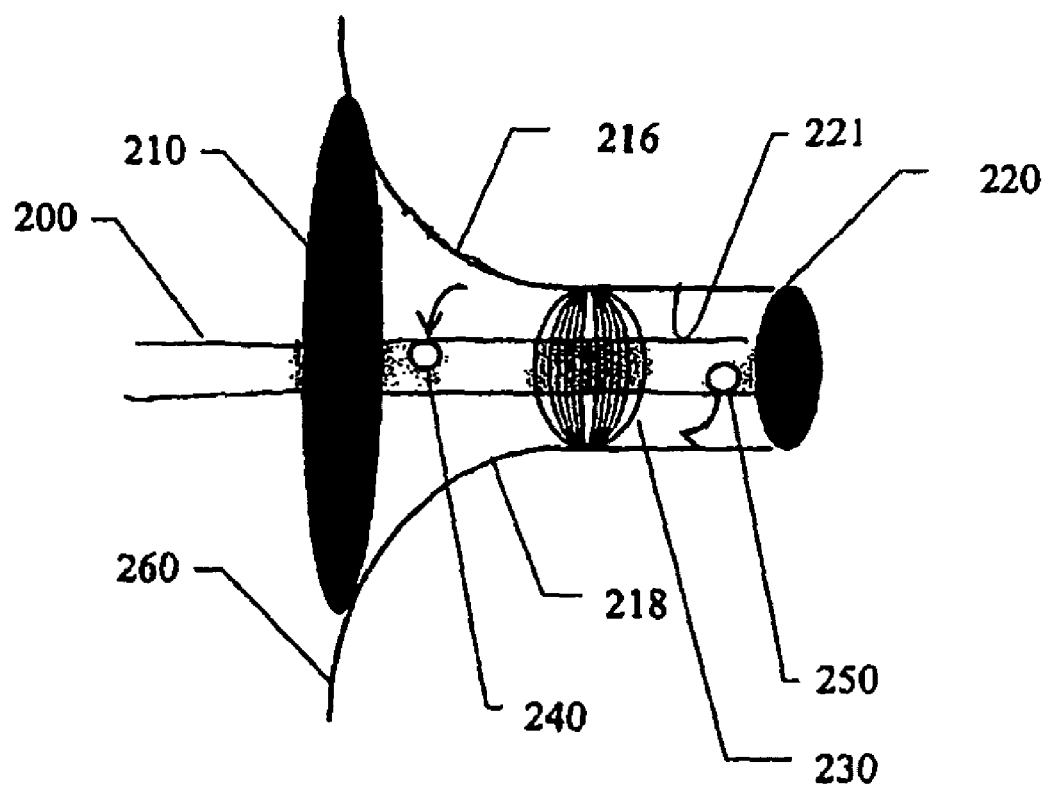

FIGS. 2D and 2E show the catheter 200 extending from the left atrium 260 into a pulmonary vein 216. In FIG. 2E, the first balloon 210 and second balloon 220 are shown in an inflated configuration. The first and second balloons 210, 220 block off a portion 218 of the blood vessel between the balloons. In an example, the second balloon 220 is positioned in the pulmonary vein 216 and the first balloon 210 is positioned in the left atrium 260 near the pulmonary vein. In an example, the catheter 200 is configured to selectively circulate one or more fluids such as blood, saline, and/or a neurotoxic solution into and out of the vessel through one or more ports. In an example, the expanded electrode 230 delivers a stimulation signal to an intravascular surface 221 of the pulmonary vein 216. In an example, the effectiveness of an agent delivered to the vessel, e.g., a neurotoxic solution, is monitored by delivering stimulation through the electrode and detecting a response.

Figure 3A:
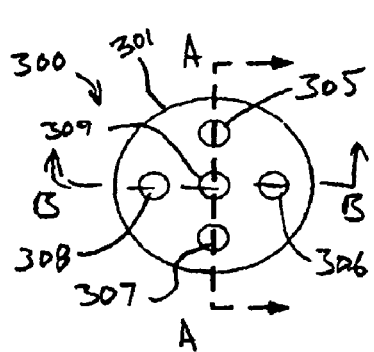
Figure 3B:
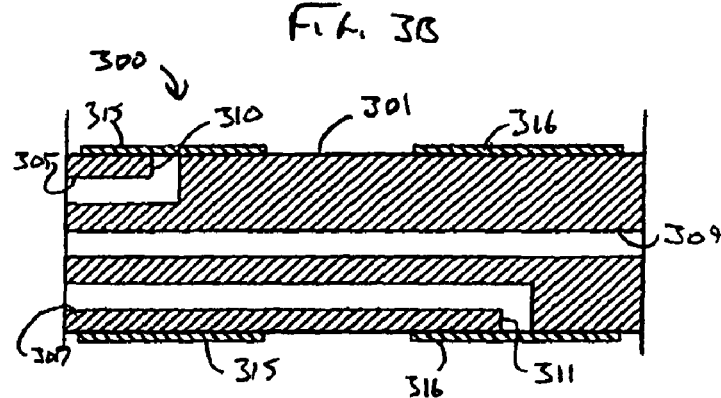
Figure 3C:
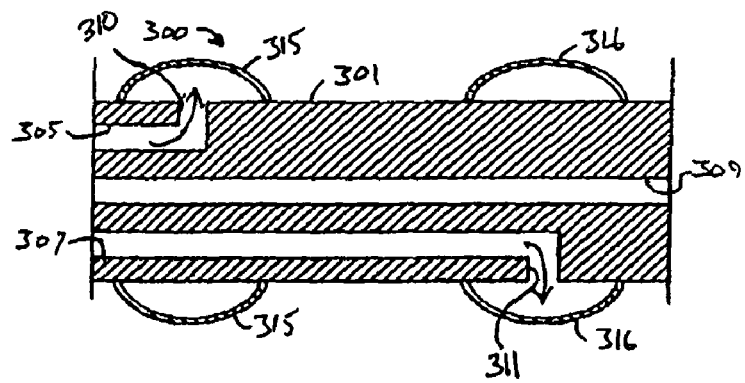

FIGS. 3A-3D illustrate lumens extending through a catheter. FIG. 3A shows an end view of a catheter 300. In an example, five lumens 305, 306, 307, 308, 309 extend through a catheter body 301. FIGS. 3B and 3C are cross-sectional side views of a portion of the catheter, taken at section A-A. FIG. 3D is a cross-sectional top view of a portion of the catheter, taken at section B-B.

Referring now to FIG. 3D, in an example, ports 326 and 328 are in communication with space around ports 317, 318. In an example, ports 326 and 328 are located between the balloons, so that when the balloons are inflated in a blood vessel, the ports are in communication with a segment of the blood vessel that is isolated by the balloons. In an example, port 326 delivers fluid to the vessel and port 328 carries fluid away from the vessel, i.e. drains the vessel. In an example port 326 delivers fluid under pressure. In an example, suction is applied to port 328. In another example, port 326 delivers fluid while port 328 drains fluid from the vessel. In an example, ports 326 and 328 flush an agent such as a neurolytic fluid from the vessel and then replace the agent with saline solution or blood. In an example, port 328 is situated closer to balloon 315 and port 326 is situated closer to port 316, so that fluid is flushed from one end of an isolated segment of a blood vessel to a second end of the isolated segment.

Referring now to FIG. 3D, in an example, ports 306 and 308 are in communication with space around ports 317, 318. In an example, ports 306 and 308 are located between the balloons, so that when the balloons are inflated in a blood vessel, the ports are in communication with a segment of the blood vessel that is isolated by the balloons. In an example, port 306 delivers fluid to the vessel and port 308 carries fluid away from the vessel, i.e. drains the vessel. In an example port 306 delivers fluid under pressure. In an example, suction is applied to port 308. In another example, port 306 delivers fluid while port 308 drains fluid from the vessel. In an example, ports 306 and 308 flush an agent such as a neurolytic fluid from the vessel and then replace the agent with saline solution or blood. In an example, port 308 is situated closer to balloon 315 and port 306 is situated closer to port 316, so that fluid is flushed from one end of an isolated segment of a blood vessel to a second end of the isolated segment.

Figure 4A:
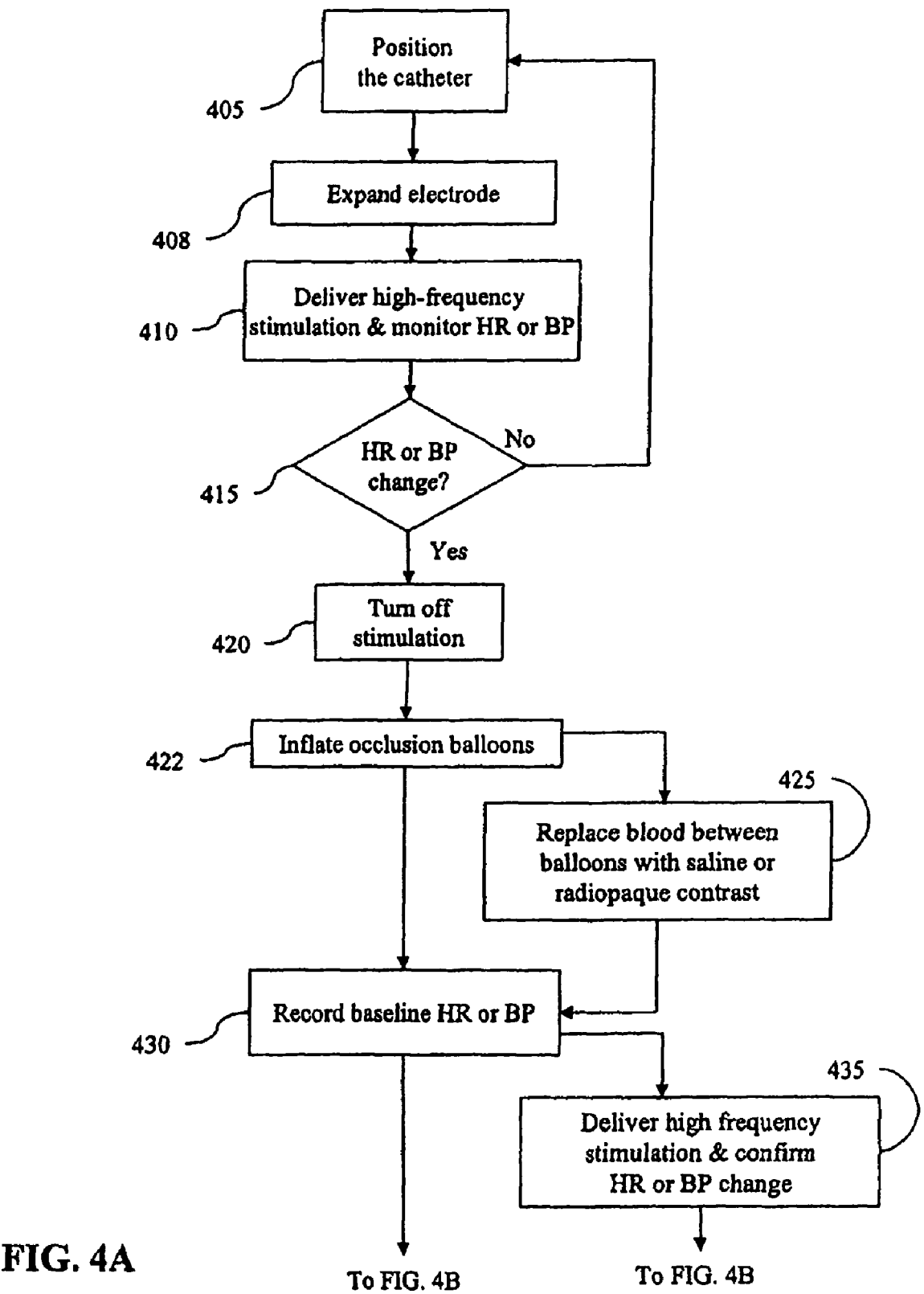
FIGS. 4A and 4B are flow charts that illustrate a method of administering neurotoxic therapy to a pulmonary vein.
Figure 4B:
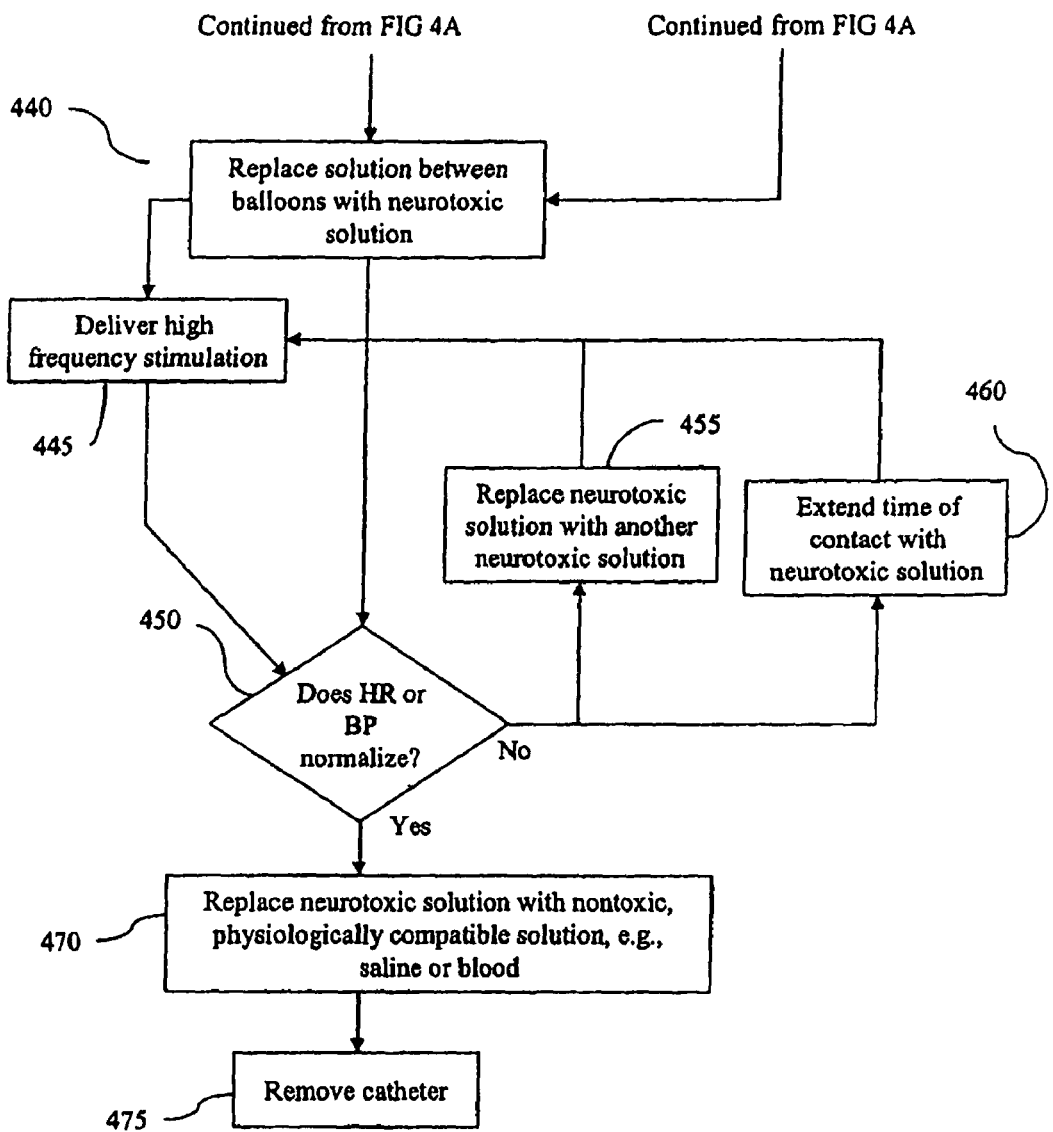

Referring now to FIGS. 4A and 4B, a method of delivering a neurotoxic treatment is shown. FIG. 4A shows a method for positioning the catheter and obtaining a baseline reading. At 405, the catheter is positioned in a blood vessel. In an example, the catheter is the catheter as shown in FIGS. 2A-E or FIGS. 3A-D. In an example, the catheter is positioned in the pulmonary vein. At 408, the expandable electrode is expanded. At 410, high frequency stimulation is delivered to an intravascular surface and the patient's heart rate or blood pressure, is monitored. In an example, both the heart rate and blood pressure are monitored. In an example, one or more other physiologic variables that are known to change with parasympathetic stimulation are also monitored. If the heart rate and/or blood pressure do not change at 415, the catheter is repositioned, at 405. In an example, the high frequency stimulation is turned off, the electrode is contracted, and then the electrode is repositioned by a physician. Once the catheter and electrode are in a position where stimulation elicits a change in the physiologic variable, the stimulation is turned off at 420 and occlusion balloons are inflated at 422. In an example, two occlusion balloons are inflated, as shown in FIG. 2C or FIG. 2E. At 425, blood in the vessel is replaced with a nontoxic physiologically compatible solution such as a saline or radiopaque contrast solution. At 430, a baseline heart rate, blood pressure, or other physiologic variable is recorded. In an alternative example, the blood is not replaced, and the method moves directly from inflating the occlusion balloons 422 to recording the baseline heart rate, blood pressure, or other physiologic variable at 430.

Referring now to FIG. 4B, at 435, optionally high frequency stimulation is delivered and a change in heart rate and/or blood pressure is confirmed. At 440, the volume in the occluded vessel between the balloons is replaced with a phenol solution or another neurotoxic agent containing solution. The neurotoxic solution is left in contact with the blood vessel for a period of time, and at 445, optionally, high frequency stimulation is applied. In another example, high frequency stimulation is not applied to the vessel. At 450, one or more physiological parameters, such as the heart rate and/or blood pressure, are analyzed to determine whether they have normalized. In an example, both the heart rate and blood pressure are analyzed. In an example, the heart rate or blood pressure normalizes when the activity of neurons innervating the region with one or more ectopic foci is inhibited or eliminated, thereby reducing or eliminating responsiveness of the region to high frequency stimulation. If the heart condition is normalized during agent administration, the agent in the vessel chamber created by balloon expansion is replaced with a nontoxic physiological compatible solution such as saline or blood 470, and the catheter is removed 475, or moved to a new location for additional treatment. In an example, if the heart rate or blood pressure is not normalized, the agent is replaced at 455, e.g., with a higher concentration of the agent. In another example, at 460 the agent is left in the vessel for an additional period of time. At 445, optionally high frequency stimulation is delivered and at 450, the heart rate or blood pressure is again analyzed to determine whether it has normalized. In an example, this cycle is repeated until sufficient neurotoxicity is achieved.

The systems and apparatus described in United States Published Patent Application Nos. 2003/0069606, 2003/0018362, 2002/0052621, and 2002/0095197 can be used with the presently described methods and systems for neurolytically treating atrial fibrillation. An example of a balloon catheter device is described in United States Published Patent Application No. 2002/0052621. A catheter balloon having a semipermeable membrane is described in United States Published Patent Application No. 2002/0095197. In another example, a catheters previously employed to deliver agents which inhibit myocytes near the pulmonary vein is used to administer an agent to the pulmonary vein. Examples of such catheters are described in Schauerte et al. (2001); Maloney et al. (1998); Pappone et al. (1999; 2000); Pappone et al., *J. Am. Coll. Cardiol.*, 42:185 (2003) and Oral et al., *Circ.*, 108:2355 (2003); Friedrich et al., *J. Thoracic. & Cardiovascl. Surg.*, 127:335 (2003) and EP384445.

Figure 5:
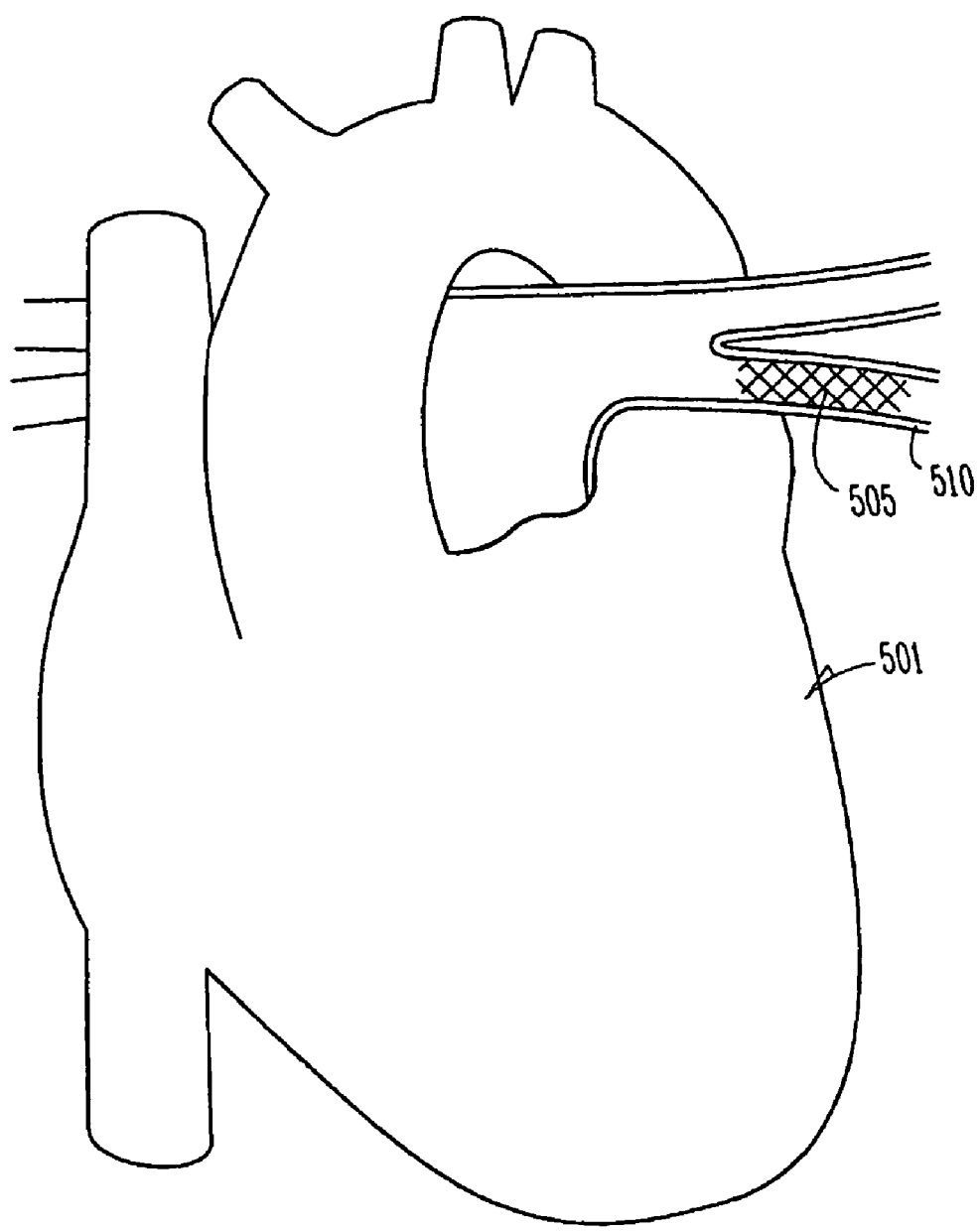
FIG. 5 is an illustration of a stent in a pulmonary vein.

In another example, a neurotoxic agent is delivered via an implanted matrix. FIG. 5 shows a heart 501 and an implanted matrix 505 such as a stent in a pulmonary vein 510. The matrix 505 contains a neurotoxic agent. The implanted matrix releases the agent by diffusion, chemical reaction, or solvent activators.

The present invention also includes a kit that includes, for example, one or more catheters, balloons, reservoirs, stents, or agents, preferably packaged in sterile condition. In an example, a kit also includes a syringe, saline, a contrast agent, and a guidewire for use with the device, preferably packaged in sterile condition, as well as written instructions for use of the devices in the kit or practice of a neurolytic treatment method.

In an example, a kit includes packing material enclosing, separately packaged, at least one implantable device adapted for the delivery of an agent, e.g., a catheter, a wrap, a stent, a shunt or a synthetic graft, and at least one unit dosage form including the agent, as well as instruction means for their use, in accord with the present methods. The unit dosage form may include an amount of at least one of the present agents effective to accomplish the therapeutic results described herein when delivered locally. In an example, a kit includes a catheter adapted for the local delivery of at least one agent to a site in the lumen of a pulmonary vein, along with instruction means directing its use in accord with the present invention. In a preferred aspect, the infusion catheter is a double balloon or quadruple balloon catheter with a permeable membrane. In another example, the kit includes a non-catheter delivery device, e.g., a wrap, a stent or shunt, for local delivery. A stent, wrap or shunt useful in the methods of the invention can include a biodegradable coating or porous non-biodegradable coating, e.g., a PTFE membrane, having dispersed therein one or more agents, optionally a sustained release dosage form of an agent of the invention.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A method for treating a patient suffering from arrhythmias, comprising:
   inserting a catheter of an apparatus into a blood vessel of the patient, wherein the apparatus comprises
   a catheter body including at least one lumen and at least one port in communication with the lumen;
   first and second inflatable balloons coupled to the catheter body, the at least one port located between the first and second balloons, wherein the second balloon is expandable and configured to block an opening between the atrium and the pulmonary vein when expanded;
   a conductor extending through the catheter body; and
   an expandable electrode coupled to the conductor and positioned between the first and second inflatable balloons, wherein the first and second inflatable balloons and the expandable electrode are arranged to allow for identifying a region in the pulmonary vein using stimulation delivered through the expandable electrode and isolating the identified region by inflating the first and second inflatable balloons for treating the atrial fibrillation in the isolated region, the region associated with the one or more ectopic foci, wherein the expandable electrode is adapted to deliver stimulation to the pulmonary vein effective to promote electrical discharge from ectopic foci, thereby altering heart rate and/or blood pressure;
   directing the catheter through the blood vessel to the pulmonary vein;
   expanding the electrode on the catheter in the pulmonary vein and applying high frequency stimulation from the electrode to a region of the pulmonary vein;
   sensing whether the high frequency stimulation alters heart rate and/or blood pressure of the patient;
   inflating the first and second balloons to isolate a region in which high frequency stimulation alters heart rate and/or blood pressure; and
   delivering at least one neurolytic or neurotoxic agent from the catheter to the isolated region in an amount effective to normalize heart rate and/or blood pressure in the patient.

2. The method of claim 1 wherein the first balloon is located at the distal end of the catheter, the first balloon expandable to block a pulmonary vein.

3. The method of claim 1 wherein the catheter body includes a first port in communication with a first lumen and a second port in communication with a second lumen, the first and second ports located between the first and second inflatable balloons adapted to deliver one or more neurolytic agents to a portion of a pulmonary vein between the first and second balloons.

4. The method of claim 1 wherein the expandable electrode includes a stent.

5. The method of claim 1 wherein the apparatus further comprises a guidewire for steerable guidance of the catheter.

6. The method of claim 1 wherein the apparatus further comprises a device coupled to the catheter body and adapted to deliver electrical stimulation signals to the expandable electrode, the device including a pump adapted to circulate an agent through the catheter body.

7. The method of claim 1 wherein the neurolytic agent comprises a local anesthetic.

8. The method of claim 7 wherein the local anesthetic comprises phenol.

9. The method of claim 1 wherein the apparatus further comprises a pump coupled to the catheter body and adapted to circulate a fluid into and out of a blood vessel through the at least one port.

10. The method of claim 1 wherein the apparatus further comprises a pump coupled to the catheter body and adapted to circulate a fluid into a blood vessel through the first port and out of the pulmonary vein through the second port.

11. The method of claim 1 wherein the first and second inflatable balloons are configured to block off the portion of the blood vessel between the first and second balloons.

12. The method of claim 1 wherein the first inflatable balloon extends over the first port, and the second inflatable balloon extends over the second port.

13. The method of claim 1 wherein the first and second inflatable balloons are independently inflatable.

14. The method of claim 1 wherein the first and second lumens are in communication with each other, and the first and second inflatable balloons are simultaneously inflatable.

* * * * *

UNITED STATES PATENT AND TRADEMARK OFFICE
CERTIFICATE OF CORRECTION

PATENT NO. : 8,052,668 B2  
APPLICATION NO. : 11/383095  
DATED : November 8, 2011  
INVENTOR(S) : Haris J. Sih Page 1 of 1

It is certified that error appears in the above-identified patent and that said Letters Patent is hereby corrected as shown below:

In column 7, line 31, below "B-B." insert -- Referring now to FIG. 3B, lumen 305 extends through the catheter body 301 to a first port 310. Lumen 307 extends through the catheter body 301 to a second port 311. A first balloon 315 extends over the first port 310. A second balloon 316 extends over the second port 311. In an example, the first balloon 315 and second balloon 316 extend around the lead body. Referring now to FIG. 3C, in an example, the first and second balloons 315, 316 can be inflated by pressurizing the first and second lumens 305, 307 with a gas or liquid that flows through lumens and ports 310, 311 to inflate the balloons. In an example, balloons 315, 316 are independently inflatable. In another example, lumens 305 and 307 are in communication with each other, so that the balloons 315, 316 inflate simultaneously. In alternative example, a single lumen having two ports is used to inflate the first and second balloons. --.

In column 7, lines 48-64, below "isolated segment." delete "Referring now to FIG. 3D, in an example, ports 306 and 308 are in communication with space around ports 317, 318. In an example, ports 306 and 308 are located between the balloons, so that when the balloons are inflated in a blood vessel, the ports are in communication with a segment of the blood vessel that is isolated by the balloons. In an example, port 306 delivers fluid to the vessel and port 308 carries fluid away from the vessel, i.e. drains the vessel. In an example port 306 delivers fluid under pressure. In an example, suction is applied to port 308. In another example, port 306 delivers fluid while port 308 drains fluid from the vessel. In an example, ports 306 and 308 flush an agent such as a neurolytic fluid from the vessel and then replace the agent with saline solution or blood. In an example, port 308 is situated closer to balloon 315 and port 306 is situated closer to port 316, so that fluid is flushed from one end of an isolated segment of a blood vessel to a second end of the isolated segment.".

Signed and Sealed this  
Thirteenth Day of March, 2012

David J. Kappos  
*Director of the United States Patent and Trademark Office*